United States Patent
Malin (10) Patent No.: US 7,314,341 B2
(45) Date of Patent: Jan. 1, 2008

(54) AUTOMATIC STORAGE DEVICE AND CLIMATE CONTROLLED CABINET WITH SUCH A DEVICE

(75) Inventor: Cosmas G. Malin, Mauren (LI)

(73) Assignee: Liconic AG, Nendelin (LI)

( * ) Notice: Subject to any disclaimer, the term of this patent is extended or adjusted under 35 U.S.C. 154(b) by 397 days.

(21) Appl. No.: 10/754,632

(22) Filed: Jan. 12, 2004

(65) Prior Publication Data

US 2004/0213651 A1    Oct. 28, 2004

(30) Foreign Application Priority Data

| Jan. 10, 2003 | (CH) | .................................... 0040/03 |
| Jan. 20, 2003 | (CH) | .................................... 0077/03 |
| May 12, 2003 | (CH) | .................................... 0824/03 |

(51) Int. Cl.
    *B65G 1/137*    (2006.01)
(52) U.S. Cl. ................................. 414/331.02
(58) Field of Classification Search ............... 414/277, 414/273, 281, 331.02, 331.05, 331.1; 312/9.6, 312/9.7
See application file for complete search history.

(56) References Cited

U.S. PATENT DOCUMENTS

| 2,321,794 | A |   | 6/1943  | Braun |
| 3,378,827 | A | * | 4/1968  | Hertrich ...................... 360/92 |
| 4,250,266 | A |   | 2/1981  | Wade |
| 4,643,879 | A |   | 2/1987  | Hanaway |
| 4,907,889 | A |   | 3/1990  | Simone |
| 4,981,409 | A |   | 1/1991  | Hirose et al. |
| 5,143,193 | A |   | 9/1992  | Geraci |
| 5,164,909 | A | * | 11/1992 | Leonhardt et al. .......... 700/215 |
| 5,220,548 | A |   | 6/1993  | Nakatsukasa et al. |
| 5,266,272 | A |   | 11/1993 | Griner et al. |
| 5,277,534 | A | * | 1/1994  | Anderson et al. ............ 414/281 |
| 5,343,403 | A |   | 8/1994  | Beidle et al. |
| 5,449,229 | A |   | 9/1995  | Aschenbrenner et al. |
| 5,470,744 | A |   | 11/1995 | Astle |
| 5,541,897 | A |   | 7/1996  | Baca et al. |
| 5,645,800 | A |   | 7/1997  | Masterson et al. |
| 5,735,587 | A |   | 4/1998  | Malin et al. |
| 6,008,964 | A | * | 12/1999 | Goodknight et al. ......... 360/92 |
| 6,059,507 | A |   | 5/2000  | Adams |
| 6,129,428 | A |   | 10/2000 | Helwig et al. |
| 6,323,035 | B1 |  | 11/2001 | Kedar et al. |
| 6,400,659 | B1 |  | 6/2002  | Kitaoka |
| 6,475,776 | B1 |  | 11/2002 | Higuchi |
| 6,478,524 | B1 |  | 11/2002 | Malin |
| 6,536,859 | B1 |  | 3/2003  | Bathe |
| 6,568,770 | B2 |  | 5/2003  | Gonsaka et al. |
| 6,669,430 | B2 | * | 12/2003 | Ostwald et al. ............. 414/277 |

(Continued)

FOREIGN PATENT DOCUMENTS

DE    197 50 912 A1    5/1999

(Continued)

*Primary Examiner*—Charles A Fox
(74) *Attorney, Agent, or Firm*—Browdy and Neimark, PLLC (57) ABSTRACT

The invention relates to a storage device and a climate controlled cabinet with a storage assembly and a transport device. For minimizing the access times, the transport device can be arranged in the center of a rotating table. The storage assembly is arranged on the rotating table, which improves access. The climate controlled cabinet is provided with an automatic door at a wall, roof or bottom thereof.

34 Claims, 7 Drawing Sheets

U.S. PATENT DOCUMENTS

| | | | |
|---|---|---|---|
| 6,669,432 B2 * | 12/2003 | Hamel et al. | 414/331.05 |
| 7,013,198 B2 * | 3/2006 | Haas | 700/218 |
| 2002/0063077 A1 | 5/2002 | Ferger et al. | |
| 2004/0004415 A1 | 1/2004 | Melching | |
| 2004/0115101 A1 | 6/2004 | Malin | |

FOREIGN PATENT DOCUMENTS

| | | |
|---|---|---|
| DE | 198 57 282 A1 | 6/2000 |
| DE | 199 36 572 A1 | 2/2001 |
| DE | 102 07 847 A1 | 8/2003 |
| EP | 0 154 538 A2 | 9/1985 |
| EP | 0 251 441 A2 | 4/1987 |
| EP | 0 251 441 A3 | 4/1987 |
| EP | 0 293 782 A1 | 12/1988 |
| EP | 0 569 214 A2 | 11/1993 |
| EP | 1 018 544 A1 | 12/2000 |
| EP | 1 256 808 A1 | 11/2002 |
| EP | 1 354 623 A1 | 10/2003 |
| FR | 2 788 042 A1 | 7/2000 |
| GB | 2 386 153 A | 9/2003 |
| WO | WO 92/14550 A1 | 9/1992 |
| WO | WO 93/09440 A1 | 5/1993 |
| WO | WO 98/05753 A1 | 2/1998 |
| WO | WO 02/059251 A2 | 8/2002 |

* cited by examiner

AUTOMATIC STORAGE DEVICE AND CLIMATE CONTROLLED CABINET WITH SUCH A DEVICE

CROSS REFERENCE TO RELATED APPLICATIONS

This application claims the priority of Swiss patent applications 0040/03, filed Jan. 10, 2003, 0077/03, filed Jan. 20, 2003 and 0824/03 filed May 12, 2003, the disclosures of which is incorporated herein by reference in their entirety.

BACKGROUND OF THE INVENTION

The invention relates to an automatic storage device and a climate controlled cabinet with a storage assembly and an automatic transport device.

Storage devices of this type are used wherever objects must be stored and accessed automatically. The range of applications covers the long-term storage of microtiterplates in substance holds as well as the short-time incubation of cell cultures or microorganisms under well defined climatic conditions. Such devices must meet high standards in compactness, throughput and access times. In addition, recent developments in the field of protein crystal growth for protein crystallography have made it desirable to keep vibrations low.

WO 98/05753 describes a storage device where the objects are stored in a carousel-like arrangement of storage towers and can be transferred between the storage towers and a defined transfer position by means of a transport lift. While the transport lift is moved vertically, the storage towers are positioned for access by rotating the carousel-like arrangement.

EP 1 074 488 shows a device where the storage towers have fixed position. This device allows a substantially vibration-free storage of the objects. A disadvantage of this solution is the fact that only a small number of storage towers can be used. If this storage device is used in a housing with a front side door, only two or three storage towers can be accessed without being obstructed by the transport lift. Hence, this device is not suited for storing a large number of objects.

BRIEF SUMMARY OF THE INVENTION

Hence, it is a general object of the invention to provide a storage device that is very compact and a climate controlled cabinet containing such a storage device.

Now, in order to implement these and still further objects of the invention, which will become more readily apparent as the description proceeds, the storage device is manifested by the features that it comprises a storage assembly with storage locations for objects to be stored, said storage assembly being arranged circularly around a central area and an automatic transport device for transporting the objects, said transport device having a manipulator arranged in said central area for moving objects into and removing objects from the storage assembly, wherein said manipulator and/or said storage assembly is or are rotatable about a rotation axis.

In a second aspect of the invention, a climate controlled cabinet with such a storage device is provided.

In both these aspects of the invention, using the central area for the manipulator provides a compact design. Still, all storage locations in the storage assembly can be accessed.

In an advantageous embodiment, the manipulator is rotatable, which makes it possible to access all storage locations without rotating the storage assembly. This allows a vibration free storage of the objects and a fast access because there is no need to rotate the heavy storage assembly. If, in addition, the storage assembly is rotatable (e.g. manually), easy manual access to all storage locations remains possible.

The storage device is also suited for storing objects of differing height.

In an advantageous embodiment, the storage assembly comprises storage towers for the objects. The storage towers can be positioned and designed such that the objects project from the storage towers towards the rotation axis, i.e. they project beyond the side walls of the storage towers. This allows to mount neighboring storage towers very close to each other and to achieve a very compact design.

Advantageously, the storage device is used in a climate controlled cabinet.

In a third aspect of the invention, a climate controlled cabinet is provided which comprises a storage assembly with storage locations for objects to be stored, an automatic transport device for transporting the objects, said transport device having a manipulator for moving objects into and removing objects from the storage assembly, an automatic door arranged in a root or bottom of said cabinet for transporting objects between a transfer position above said cabinet and said storage device, and a telescope mechanism for vertically moving said manipulator through said automatic door.

Using a telescope mechanism allows to transport the objects through the door in the roof or bottom of the cabinet while still keeping the height of the cabinet small.

BRIEF DESCRIPTION OF THE DRAWINGS

The invention will be better understood and objects other than those set forth above will become apparent when consideration is given to the following detailed description thereof. Such description makes reference to the annexed drawings, wherein.

DETAILED DESCRIPTION OF THE INVENTION

Figure 1A:
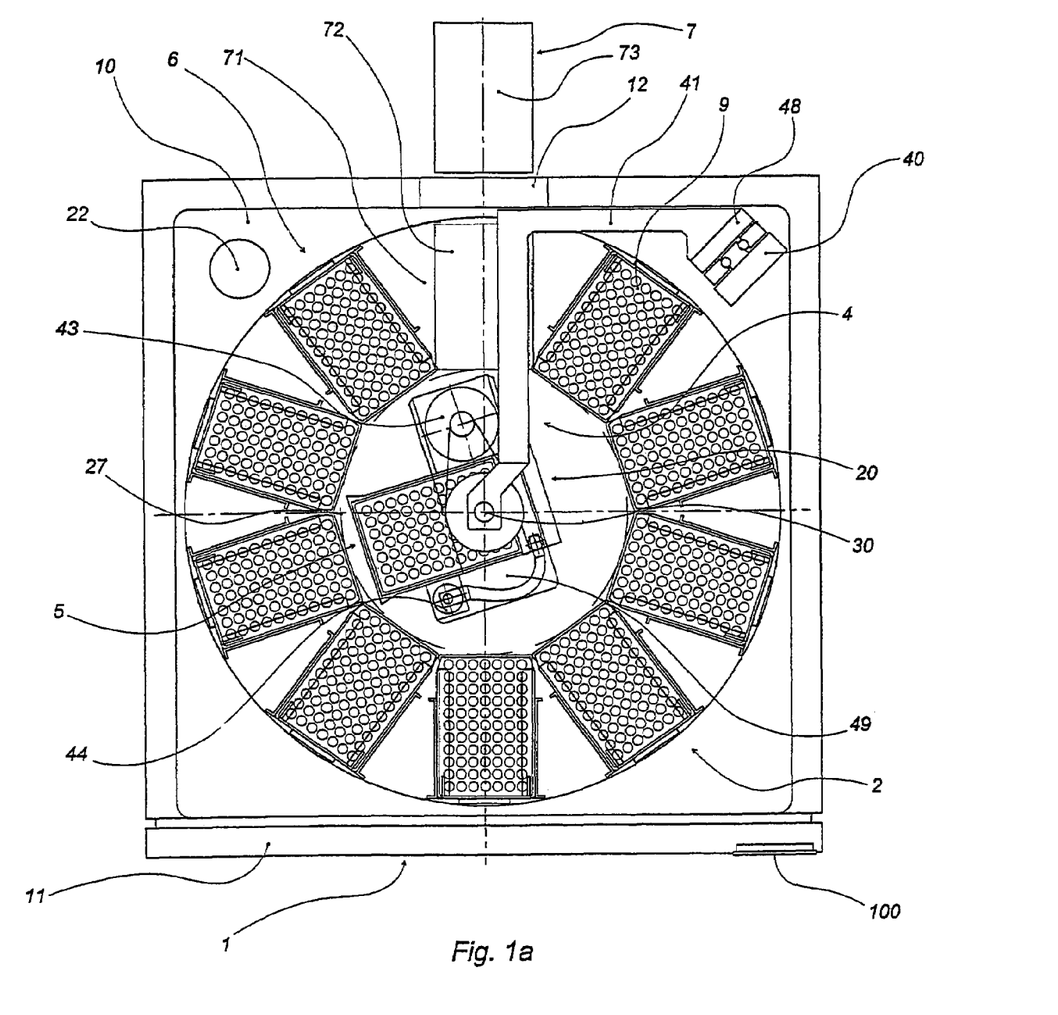
FIG. 1a shows a top view of an embodiment of the storage device arranged in a climate controlled cabinet.

FIG. 1a shows an embodiment of a climate controlled cabinet 1 with a storage device 2 in top view. Storage device 2 comprises several storage towers 6, each of which has several storage positions for receiving the objects 9 on top of each other, and a transport device 4, which automatically transports the objects from an external transfer position 73 to an arbitrary storage location within a storage tower 6 or vice versa. Transport device 4 comprises a transfer device 7, which can be arranged stationary at the location of external transfer position 73 or be movable between external transfer position 73 and an inner transfer position 72.

An automatic door 12 is located at the back of the climate controlled cabinet, through which the objects are passing when being automatically transported to and from the storage device. A user door 11 is provided for manual access to the storage towers 6. The size of the user door corresponds substantially to a side of the cabinet.

The storage towers 6, which form the storage assembly of the storage device, are arranged concentrically around a rotation axis 30 on a rotatable table 20. The storage towers are distributed substantially regularly over 360° on a circle (with the possible exception of a gap described below, wherein a width of this gap corresponds substantially to the width of a single storage tower). The storage towers 6 comprise an open side 68 (cf. FIGS. 3a, 3b) facing rotation axis 30 and being used for inserting and removing the objects. The ring formed by the storage towers 6 has a gap 71. In a central area 27 surrounded by the storage towers there is a lift carriage 5 of the transport device. The transport device further comprises a lift tower 40, to which the vertically displaceable lift carriage 5 is mounted by means of a lift plate 49 on a support arm 41. Lift plate 49 carries a radially displaceable scoop 46 (cf. FIG. 1c) and can be rotated about rotation axis 30 by means of a rotation drive 43. Scoop 46 is moved by means of a scoop drive 44. Rotation drive 43 is mounted to lift plate 49 at the upper end of central area 27 and is used to position scoop 46 in front of the appropriate storage tower 6. For this purpose, rotation drive 43 engages a stationary cogwheel 47. Lift carriage 5 can be positioned in height by means of a lift drive 48. Rotatable table 20 can be positioned by an optional rotatable table drive 22.

Scoop 46 and scoop drive 44 form a manipulator, by means of which, as shown below, the objects 9 can be removed from or inserted into the storage assembly. The manipulator can be rotated around rotation axis 30 about at lest 200°, advantageously about substantially 360°.

The components of transport device 4 are arranged such the space in central area 27 is well used. Lift tower 40 and lift drive 48 are arranged in an otherwise unused corner of the interior space 10 of the storage device. In automatic operation, rotatable table 20 is positioned such that support arm 41 can be vertically displaced in gap 71 between the storage towers 6. The storage towers 6 and rotatable table 20 are, once positioned, stationary, and the table is only rotated in case of manual access, e.g. when storage towers have to be moved through the front door. In that case the lift carriage is moved to its topmost position such that the storage towers 6 can move below support arm 41.

When removing an object from a storage tower 6, rotation drive 43 positions scoop 46 in front of open side 68 of the storage tower, while lift drive 48 positions scoop 46 below the support face of the object. Scoop drive 44 extends scoop 46 below the object. Lift carriage 5 is lifted somewhat for engaging the object by means of scoop 46, and scoop 46 is retracted. Lift carriage 5 is positioned vertically and rotationally to be brought in alignment with inner transfer position 72, where the object is transferred to transfer device 7. Transfer device 7 moves the object to external transfer position 73, where an external system can access the object.

Figure 1B:
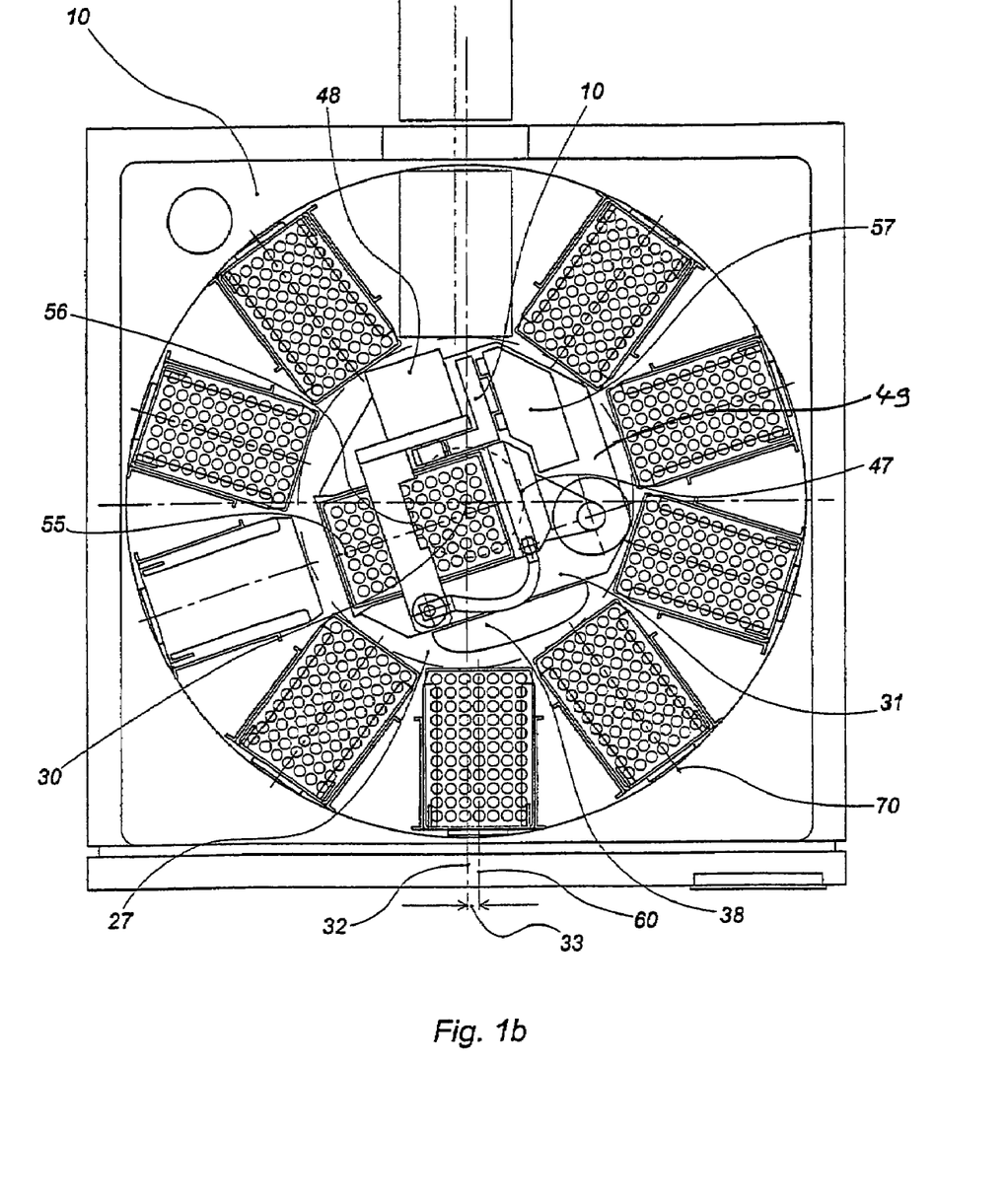
FIG. 1b shows the top view of a second embodiment of the storage device with rotatable lift tower.

FIG. 1b shows a further embodiment of a device according to the present invention. Here, the components of the transport device and the storage assembly are positioned advantageously thus that substantially the complete transport device is arranged in inner area 27. For this purpose, the storage towers 6 are tangentially offset by an offset 33. The symmetry axes or central axes 60 of the storage positions are parallel to and at distance corresponding to offset 33 from radial axes 32, which radial axes 32 extend horizontally and intersect with rotation axis 30. This allows to position the central axis of scoop 30 at said offset from rotation axis 30, which leaves more space on one side of the scoop for other components. Lift tower 40 and lift drive 48 are located immediately adjacent to lift plate 49. Rotation drive 43 rotates a base plate 31 of the lift together with lift tower 40, lift carriage 5 and rotation drive 43 about rotation axis 30. Base plate 31 can be rotated in a first rotational bearing 54. A second upper bearing 51 holds the transport device at its top end. In order to avoid vibrations during rotation, a counterweight 38 is mounted to base plate 31. By means of a second counterweight in the upper section of the lift, a dynamic balancing can be achieved. In general, a balancing of the rotated parts can be achieved by means of counterweights or a suitable arrangement of individual components.

Figure 1C:
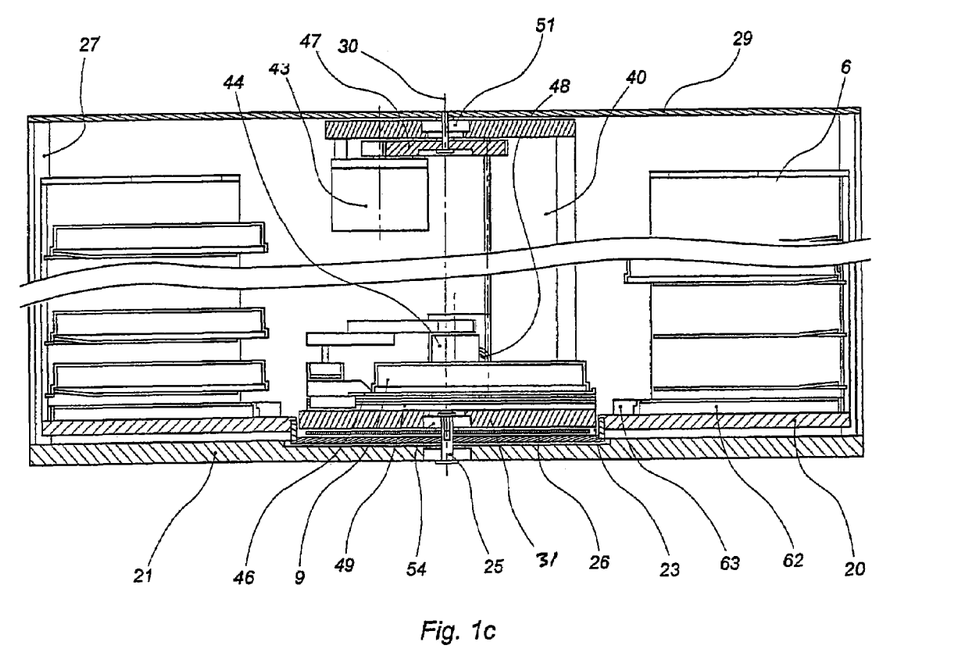
FIG. 1c shows a front view and partially sectional view of the storage device with rotatable lift tower.

FIG. 1c shows a front view in partially sectional view of the previous embodiment. For the scoop to be able to load up the lowest objects in the storage towers, rotatable table 20 and the base plate comprise a recess 23 for receiving lift carriage 5 in its lowest position, i.e. recess 23 (or a suitable opening in rotatable table 20) receives a part of the transport device in this position. In order to optimally use the full height of the storage towers, rotation drive 43 is arranged in the topmost part of the storage device. Additional height is won by means of a recess 56 in the yoke of the lift carriage for receiving cogwheel 47 (cf. FIG. 1b). Rotation drive 43 is arranged such that is uses otherwise unused space on the lift carriage.

Figure 2A:
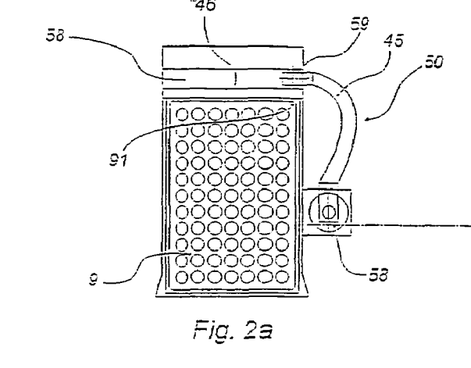
FIG. 2a shows a first embodiment of a scoop drive.

FIG. 2a shows a detail of the scoop drive in retracted position. Scoop 46 is arranged on a linear bearing 39 and can be displaced radially in respect to rotation axis 30. A curved, pivotal arm 45 is provided for moving scoop 46. One end of pivotal arm 45 is mounted to the shaft of scoop drive 44. Pivotal arm 45 can be pivoted by approximately 180°. The second end of pivotal arm 45 is mounted to an arm guide 59. Arm guide 59 runs in a notch or groove 58 arranged transversally to the direction of extension of the scoop and is located at a rear end thereof. When scoop drive 44 pivots pivotal arm 45, scoop 46 is extended or retracted.

Figure 2B:
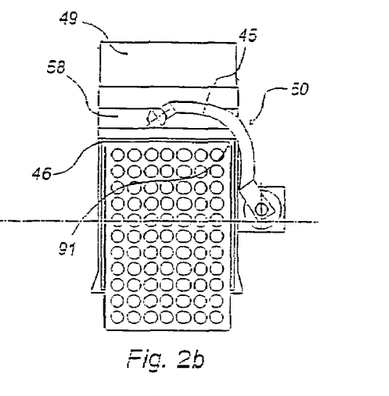
FIG. 2b shows the first embodiment of the scoop drive with partially extended scoop.

FIG. 2b shows the scoop in slightly extended position. In order to prevent a collision, pivotal arm 45 (which is at the same height as the object) is curved, i.e. it is bent or angled.

Using pivotal arm 45 for moving scoop 46 has the advantage that a soft acceleration and deceleration is achieved automatically. Furthermore, this solution is insensitive to dirt and freezing.

Finally, the scoop drive is stationary, i.e. not arranged on the scoop itself, which makes it unnecessary to provide a movable energy feed from the carriage to the drive.

Figure 2C:
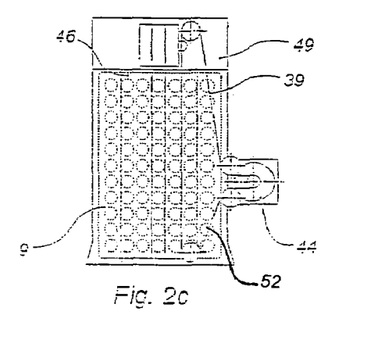
FIG. 2c shows a second embodiment of a scoop drive.

FIG. 2c shows a further embodiment of a scoop drive which uses e.g. a toothed belt 52 or any other suitable type of belt for driving the scoop. Toothed belt 52 is guided over four guide rolls and over a driving roll in such a manner that is runs at, least in one section, substantially parallel to the guide of the scoop, i.e. to the direction of extension of the scoop. In this section, toothed belt 52 is coupled to the scoop such that it can extend and retract it. Also in this solution the scoop drive is stationary.

Figure 2D:
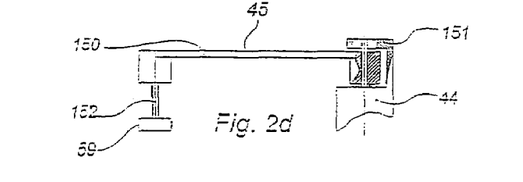
FIG. 2d shows a third Embodiment of a scoop drive.

FIG. 2d shows an embodiment with a straight pivotal arm. In order to avoid a loss of height caused by the motion of the pivotal arm over the object, pivotal arm 45 is designed such that it has a recess 150 where it is moved over the object. Since pivotal arm 45 extends far, a yoke 151 for increasing the stability is arranged at the scoop drive. A rod 152 is provided for connecting arm 45 to arm guide 59 below it.

Figure 3A:
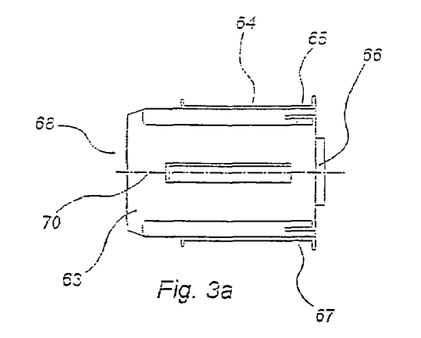
FIG. 3a shows the top view of an embodiment of a storage tower.

FIG. 3a shows a top view of a storage tower. Two lateral walls 67 and a back wall 66 are mounted to a bottom 63 of the storage tower. The side 68 opposite to back wall 66 is open. Shelves or ledges 64 are arranged in pairs on the lateral walls 67 for supporting the objects. In horizontal direction, the objects are restrained by the lateral walls 67 and back wall 66. In order to prevent the objects from inadvertently sliding out through the open side 68 of the storage tower, tongues 65 formed at the end of the ledges of shelves 64 are provided. Each tongue forms a ramp such that an object being inserted into the storage location moves up the ramp and fall back down when it reaches an end thereof.

The horizontal lengths of the lateral walls 67 and ledges or shelves 64 are such that the stored objects project freely from the storage tower towards rotation axis 30. The lateral walls 67 and ledges or shelves 64 are that much shorter that the distance between the side walls of neighboring storage towers is equal to or larger than the distance between the center most ends 92 of neighboring objects 9. This allows an optimized usage of available space.

Figure 3B:
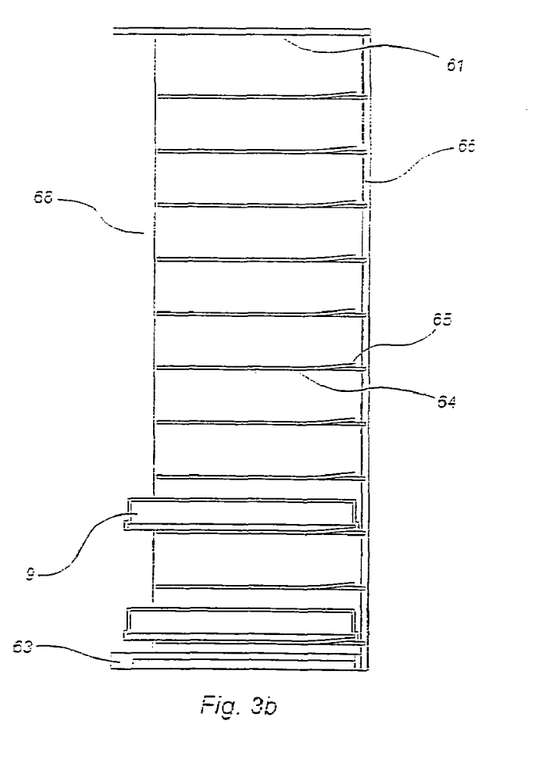
FIG. 3b shows a lateral view of the storage tower of FIG. 3a, FIG. 4a shows a lateral view of an embodiment of a horizontally displaceable transfer device.

FIG. 3b shows a lateral view of a storage tower 6. It comprises a grip plate 61, to which the lateral walls 67 and the back wall 66 are mounted at their top ends. Each tongue 65 is formed by a bent up section of the corresponding ledge or shelve 64 at the rear end thereof, i.e. at the end of the ledge or shelve 64 facing away from open side 68. The end of each tongue 65 forms an edge which rests against an inner side of the stored object. Other embodiments of suitable retaining means, such as pressed-in, wedge-shaped elements, can be used as well.

The following figures show embodiments for transferring the objects to the external transfer position 73.

Figure 4A:
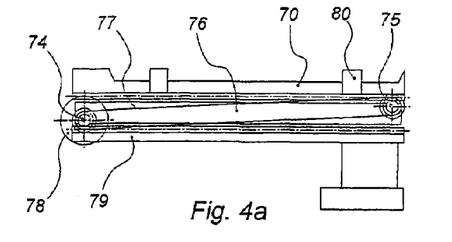

FIG. 4a shows an embodiment of a horizontally displaceable transfer device in the form of a telescope mechanism. A transfer plate 70 can be moved linearly on a carriage 76. Transfer plate 70 carries the object, which is secured against sliding off by means of a centering member 80.

Carriage 76 can in turn be moved on a stationary transfer base 79 by means of a drive wheel 74 connected to a transfer drive 78. The transfer plate is driven by a second rive wheel 75. Both drive wheels are arranged on the carriage and synchronously coupled to each other by means of a belt 77. This allows to displace the transfer device over a comparatively large distance without any need for any guide members to extend beyond the base area of the device.

Figure 4B:
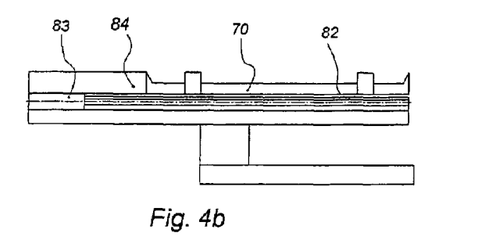
FIG. 4b shows a lateral view of a second embodiment of a horizontally displaceable transfer device.

In the transfer device of FIG. 4b, a transfer sleigh 83 is mounted to a transfer guide 82. The distance covered by the transfer plate is increased by mounting the transfer sleigh to a rear end of the transfer plate and by prolonging the transfer plate at its rear side, by means of a plate 84.

Figure 4C:
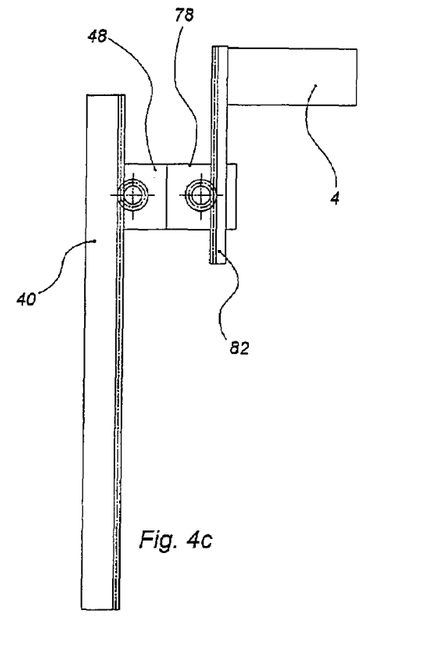
FIG. 4c shows a lateral view of an embodiment of a vertical transfer device for transferring the objects vertically.

FIG. 4c shows an embodiment where the objects are moved to the external transfer position in vertical direction. In this embodiment, a transfer guide 82 is mounted to lift carriage 48 and vertically displaceable thereto. By moving—by means of a transfer drive—the transfer guide 82 upwards and by bringing lift carriage 48 to its topmost position, the scoop can be extended in telescope-like fashion, e.g. to be moved through an automatic door in the roof of an enclosing cabinet.

Figure 4D:
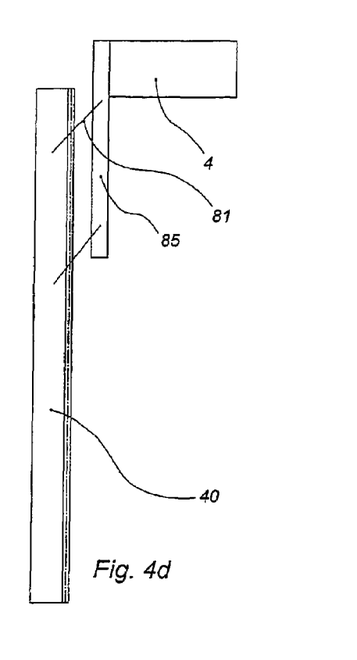
FIG. 4d shows a lateral view of a second embodiment of a vertical transfer device for transferring the objects vertically.

A further embodiment where the objects are transferred to the external transfer position in vertical direction is shown in FIG. 4d. A lift extension 85 is implemented by means of a pair of pivoting arms 81 connected to lift tower 40 and forming a parallelogram. A drive (not shown) can be used for telescopically moving the scoop upwards.

Figure 4E:
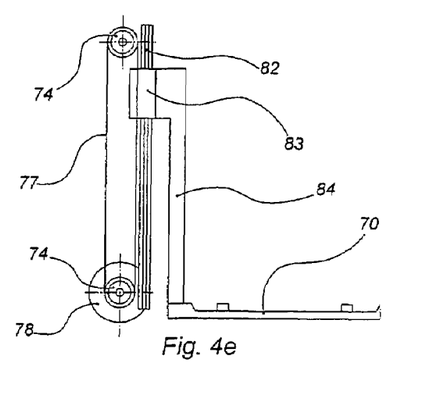
FIG. 4e shows a lateral view of a third embodiment of a vertical transfer device for transferring the objects vertically.

The embodiment shown in FIG. 4e can also be used to move the object vertically to the external transfer position. In this embodiment, a transfer device separate from and arranged higher the lift (e.g. mounted to the roof of a climate controlled cabinet) is provided for moving the object from the inner to the exterior transfer position. Transfer plate 70 is arranged at the bottom end of a transfer extension 84. The top end of the transfer extension is connected to transfer sleigh 83. Transfer sleigh 83 runs in a vertically extending transfer guide 82 and is driven by a belt 77. A threaded shaft can also be used for driving sleigh 83.

Figure 5:
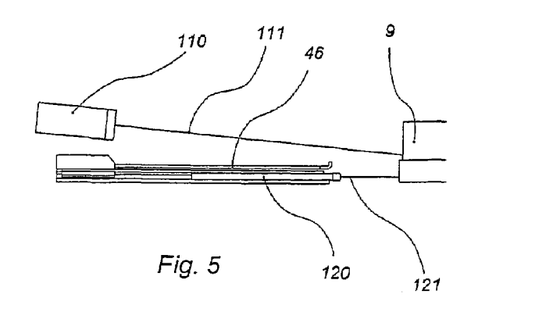
FIG. 5 shows a lateral view of an embodiment having a barcode reader and a plate sensor for keeping inventory.

It is especially advantageous to mount a reader for recognizing and identifying the objects 9 on lift carriage 5. Such a device is shown in FIG. 5. A plate sensor 120 is arranged at scoop 46, the plate reader beam 121 of which extends parallel to the direction of extension of the scoop. Furthermore, a bar code reader 110 is also mounted to lift carriage 5, which is able to read a bar code applied to an edge of the object. By combining the bar code reader with a plate sensor, the whole contents of the storage—even if a bar code is missing or unreadable—can be handled. The plate sensor further allows to prevent collisions in case of a failed access by testing for the presence or absence of an object before extending the scoop.

Figure 1D:
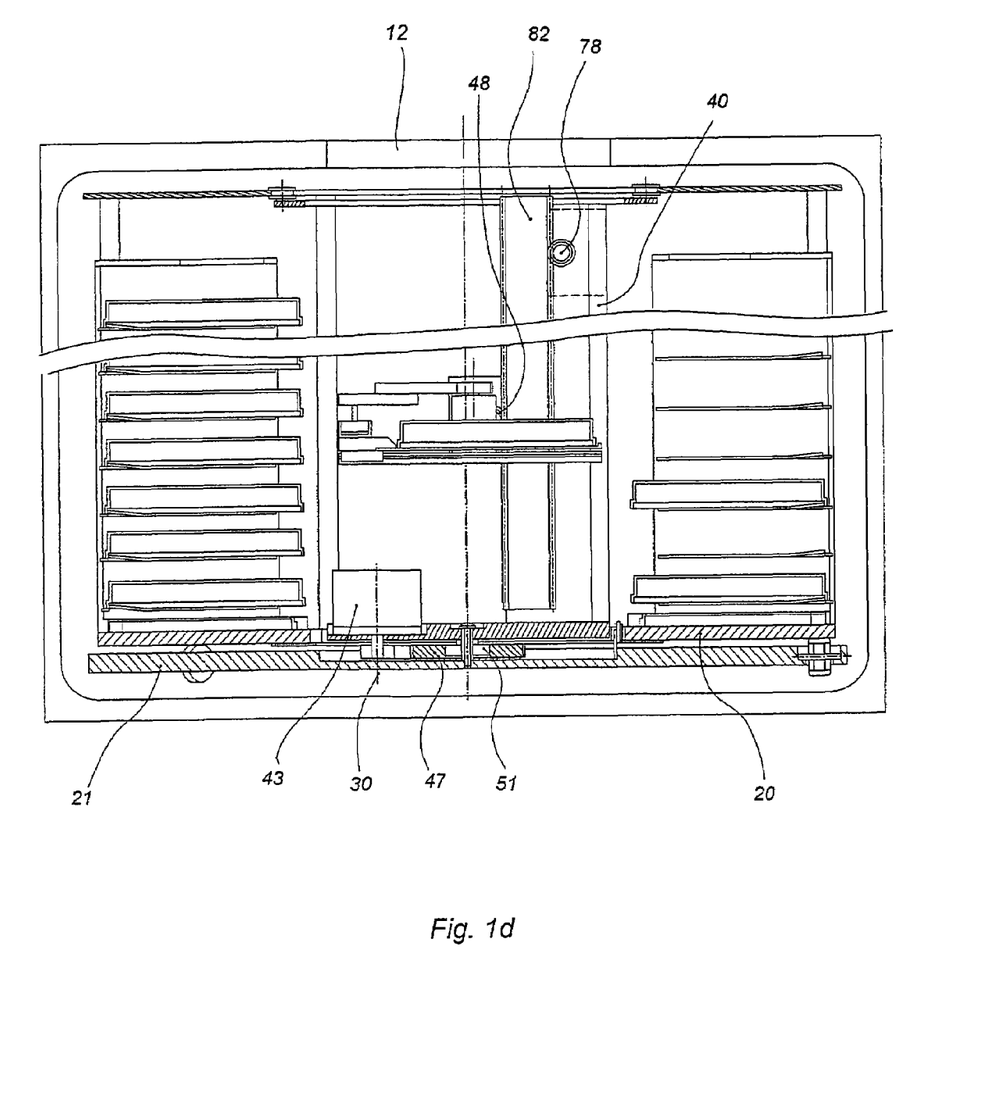
FIG. 1d shows a vertical sectional view of an embodiment of a climate controlled cabinet with automatic door in the roof.
Figure 6:
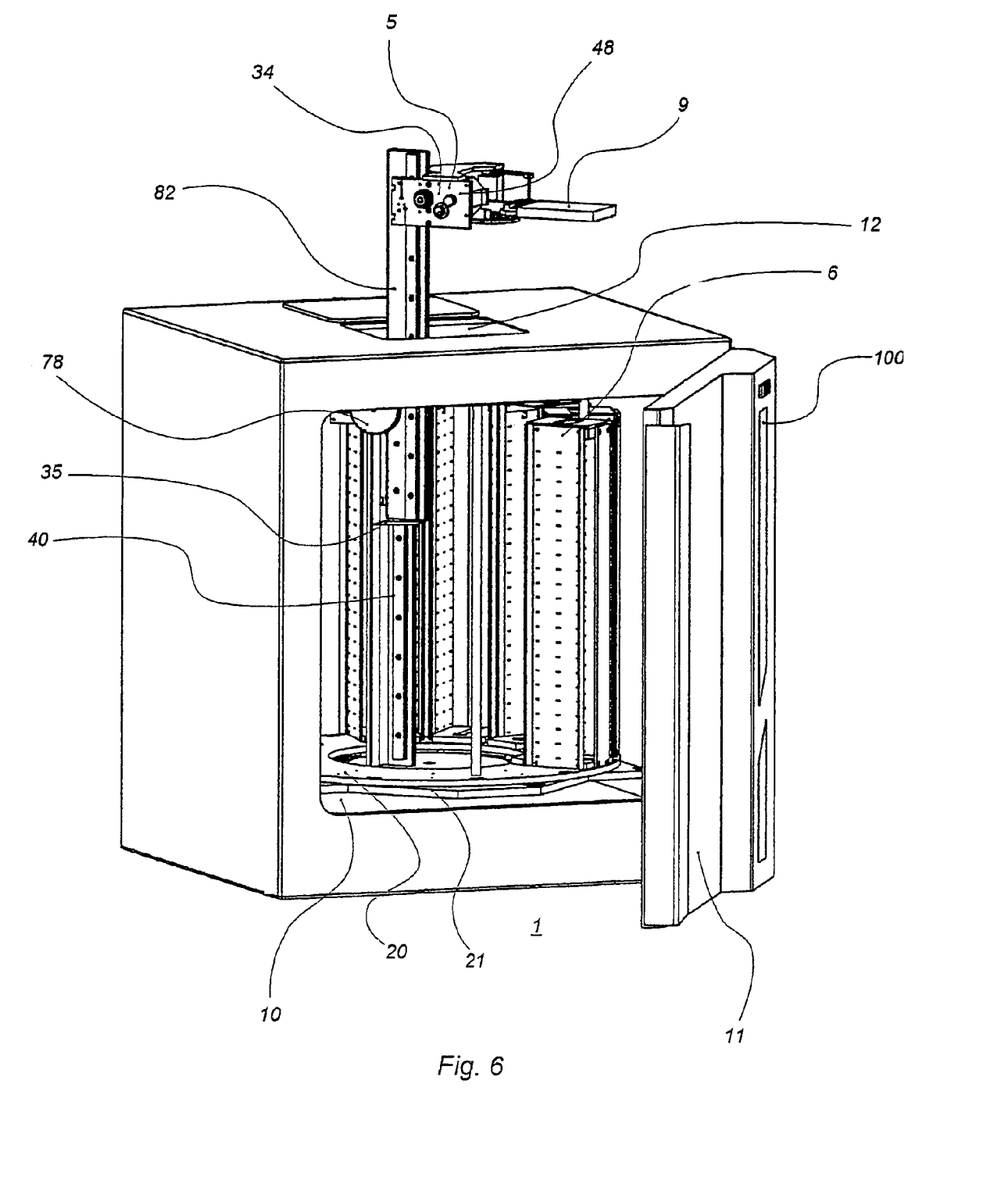
FIG. 6 shows an embodiment of a complete device with vertical transfer through the roof.

FIGS. 1d and 6 show a climate controlled cabinet equipped with the usual control and interface devices. In particular, it can comprise an alphanumeric display 100 for displaying status messages, error messages or such. The messages can originate from a control unit of the climate controlled cabinet or from an external system connected to the cabinet through an interface.

The cabinet shown in these figures has an external transfer position on top of it. For this purpose, a telescope mechanism is provided for moving the manipulator vertically out of the cabinet, which allows to keep the height of the device low. In the shown embodiment, a transfer guide 82 is mounted to lift tower 40 and is displaceable vertically thereto. Lift carriage 5 is in turn mounted to transfer guide 82 and vertically displaceable thereto. Transfer guide 82 is moved through an automatic door 12 in the roof of the cabinet. A transfer drive 78 for driving the transfer guide 82 is in frictional contact with lift tower 40.

The described telescope mechanism for vertically transferring the objects 8 can also be used in climate controlled cabinets where the storage towers are not arranged in a circle, such as the climate controlled cabinets described in U.S. Pat. No. 6,478,524.

The lift drive is arranged on transfer guide 82. The lift drive has a reduction gear 34, which is implemented as a toothed belt. The reduction gear 34 obviates the need for a vertically moving counterweight In addition to this, the friction in the reduction gear breaks the fall of lift carriage 5 in case of a power loss in such a manner that an allowable downward velocity is not exceeded. A stop 35 at the bottom end of the transfer guide 82 prevents the lift carriage 5 from falling out at the bottom.

Lift carriage 5 can be rotated at the height of the external transfer position, which allows to use a plurality of external transfer positions.

The automatic door 12 can also be mounted to the bottom of the climate controlled cabinet. In this case, the external transfer position is below the cabinet.

In the embodiments shown so far, the manipulator is rotatable automatically and the storage device is rotatable manually. It is, however, also possible to arrange the storage assembly in fixed manner, or to make it rotatable automatically. If the storage assembly is rotatable automatically, an automatic rotation of the manipulator is not strictly necessary.

While there are shown and described presently preferred embodiments of the invention, it is to be distinctly understood that the invention is not limited thereto but may be otherwise variously embodied and practiced within the scope of the following claims.

The invention claimed is:

1. A storage device comprising
    a storage assembly with storage locations for objects to be stored, said storage assembly being arranged circularly around a central area,
    an automatic transport device for transporting the objects, said transport device having
    a) a manipulator arranged in said central area for moving objects between the storage locations and an inner transfer position, said manipulator comprising a scoop for loading up said objects, a scoop drive for extending said scoop below said objects, a rotation drive for rotating said scoop about a vertical rotation axis and a lift drive for vertically displacing said scoop, and
    b) a transfer device spaced apart from said manipulator having a transfer drive for transporting said objects between the inner transfer position within said storage assembly and an external transfer position outside said storage assembly.

2. The storage device of claim 1 wherein said manipulator and said storage assembly are rotatable about the rotation axis.

3. The storage device of claim 1 wherein a gap is arranged in said storage assembly and wherein said transport device is adapted for transferring objects through said gap for transporting said objects between an external transfer position and said storage assembly.

4. The storage device of claim 1 wherein said storage assembly comprises a plurality of storage towers, each storage tower comprising a plurality said storage location above each other and being separately removable from said storage system.

5. The storage device of claim 1 wherein said manipulator is rotatable about the rotation axis.

6. The storage device of claim 5 wherein said manipulator is rotatable by at least 200° about the rotation axis.

7. The storage device of claim 1 wherein said storage assembly is mounted on a rotatable table, wherein a recess or opening is provided at a center of said table for receiving part of said transport device.

8. The storage device of claim 1 wherein said manipulator comprises
    a driving belt for extending said scoop, wherein said driving belt extends, in at least one section, substantially parallel to a direction of extension of said scoop, and is connected to said scoop in said section,
    wherein said scoop drive is adapted to driving said belt.

9. The storage device of claim 1 wherein said transport device comprises
    a lift tower arranged,
    a lift carriage arranged inside said central area, being mounted to and vertically displaceable along said lift tower and carrying said manipulator,
    a reduction gear driven by said lift drive,
    wherein said lift drive is mounted to said lift carriage.

10. The storage device of claim 9 wherein said reduction gear comprises a belt.

11. The storage device of claim 1 wherein said manipulator and any further rotating parts of said transport device are balanced in view of rotations around said rotation axis.

12. The storage device of claim 11 comprising a counterweight for balancing said manipulator and any further rotating parts of said transport device in respect to rotations about said rotation axis.

13. The storage device of claim 1 further comprising a bar code reader and/or an object sensor, at least one reading beam of which is directed parallel to a direction of extension of the scoop of said manipulator.

14. A storage device comprising
    a storage assembly with storage locations for objects to be stored, said storage assembly being arranged circularly around a central area, wherein said storage assembly comprises a plurality of storage towers, each storage tower comprising a plurality said storage location above each other and being separately removable from said storage system,
    an automatic transport device for transporting the objects, said transport device having a manipulator arranged in said central area for moving objects into and removing objects from the storage assembly, said manipulator comprising a scoop for loading up said objects, a scoop drive for extending said scoop below said objects, and a lift drive for vertically displacing said scoop thereby engaging said object by means of said scoop,
    wherein said manipulator and/or said storage assembly is or are rotatable about a rotation axis,
    and wherein said storage towers are designed and arranged such that, in said storage locations, said objects project from said storage towers towards said rotation axis.

15. The storage device of claim 14 further comprising a transfer device spaced apart from said manipulator for transporting said objects between an inner transfer position within said storage assembly and an external transfer position outside said storage assembly.

16. The storage device of claim 15 wherein said transfer device is adapted to move said objects horizontally.

17. The storage device of claim 15 wherein said transfer device is adapted to move said objects vertically.

18. The storage device of claim 14 wherein said manipulator is adapted to move said objects from and/or to an external transfer position outside said storage assembly.

19. The storage device of claim 14 wherein said manipulator is adapted to move said objects vertically from and/or to an external transfer position outside said storage assembly.

20. The storage device of claim 14 wherein said storage locations comprise central axes extending parallel to and at a given horizontal distance from radial axes, wherein said radial axes extend horizontally and intersect with said rotation axis.

21. The storage device of claim 20 wherein a central axis of said scoop is at the given horizontal distance from said rotation axis.

22. The storage device of claim 14 wherein said storage towers comprise lateral walls that are shorter than said objects.

23. The storage device of claim 14 wherein each storage towers comprises ledges for receiving said objects, wherein at least part of said ledges comprise retaining means at an end remote from said rotation axis for retaining said objects in said storage locations.

24. The storage device of claim 14 wherein each storage towers comprises ledges for receiving said objects, wherein at least part of said ledges comprise a ramp at an end remote from said rotation axis such that an object being inserted into said storage location moves up said ramp to fall back down when it reaches an end thereof.

25. A climate controlled cabinet comprising the storage device of claim 14 wherein said storage assembly is arranged on a table and wherein said climate controlled cabinet comprises a table drive for rotating said table about said rotation axis, and wherein said manipulator is rotatable about a rotation axis.

26. The climate controlled cabinet of claim 25 comprising an automatic door for transporting objects between a transfer position outside said cabinet and said storage device.

27. The climate controlled cabinet of claim 26 wherein said automatic door is arranged in a roof or bottom of said cabinet.

28. The climate controlled cabinet of claim 27 further comprising a mechanism for moving said manipulator through said automatic door.

29. A storage device comprising
a storage assembly with storage locations for objects to be stored, said storage assembly being arranged circularly around a central area,
an automatic transport device for transporting the objects, said transport device having a manipulator arranged in said central area for moving objects into and removing objects from the storage assembly,
wherein said manipulator and/or said storage assembly is or are rotatable about a rotation axis and
wherein said transport device comprises a rotation drive having a first cogwheel and a second cogwheel fixed on the storage device which engages the first cogwheel to rotate the transport device about the rotation axis when the rotation drive is rotatable about said rotation axis and the cogwheel stationary.

30. A storage device comprising
a storage assembly with storage locations for objects to be stored, said storage assembly being arranged circularly around a central area,
an automatic transport device for transporting the objects, said transport device having a manipulator arranged in said central area for moving objects into and removing objects from the storage assembly,
wherein said manipulator and/or said storage assembly is or are rotatable about a rotation axis, and
wherein said manipulator comprises
a horizontally extendible scoop,
a curved, pivotal arm for actuating said scoop, and
a scoop drive arranged laterally to said scoop for pivoting said arm,
wherein said arm is curved for preventing a collision between said arm and an object on said scoop.

31. The storage device of claim 30 wherein wherein said arm is slideably arranged in a guide, said guide extending transversally to a direction of extension of said scoop.

32. A climate controlled cabinet comprising
a storage assembly with storage locations for objects to be stored, said storage assembly being arranged circularly around a central area,
an automatic transport device for transporting the objects, said transport device having a manipulator arranged in said central area for moving objects into and removing objects from the storage assembly,
wherein said manipulator and/or said storage assembly is or are rotatable about a rotation axis.
a lift tower, a member arranged vertically displaceably on said lift tower and a lift carriage arranged vertically displaceably on said member.

33. The climate controlled cabinet of claim 32 further comprising a user door having a size corresponding substantially to a side of said cabinet.

34. A climate controlled cabinet comprising
a storage assembly with storage locations for objects to be stored,
an automatic transport device for transporting the objects, said transport device having a manipulator for moving objects into and removing objects from the storage assembly,
an automatic door arranged in a roof or bottom of said cabinet for transporting objects between a transfer position above said cabinet and said storage device,
a mechanism for vertically moving said manipulator through said automatic door, said mechanism comprising a lift tower, a member arranged vertically displaceably on said lift tower and a lift carriage arranged vertically displaceably on said member, wherein said lift carriage carries said manipulator.

* * * * *